United States Patent
Anderson

(10) Patent No.: US 8,597,340 B2
(45) Date of Patent: Dec. 3, 2013

(54) TORQUE MECHANISM ACTUATED BIOABSORBABLE VASCULAR CLOSURE DEVICE

(75) Inventor: James Anderson, Minneapolis, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 145 days.

(21) Appl. No.: 13/218,678

(22) Filed: Aug. 26, 2011

(65) Prior Publication Data
US 2012/0071910 A1    Mar. 22, 2012

Related U.S. Application Data

(60) Provisional application No. 61/383,827, filed on Sep. 17, 2010.

(51) Int. Cl.
*A61F 2/06* (2013.01)
(52) U.S. Cl.
USPC .......................................... 623/1.11; 606/198
(58) Field of Classification Search
USPC ............. 623/1.11, 1.12, 1.15, 1.18, 1.2, 1.21, 623/1.22, 23.7; 606/108, 151, 157, 191, 606/194, 198, 213; 128/831, 898
See application file for complete search history.

(56) References Cited

U.S. PATENT DOCUMENTS

| | | |
|---|---|---|
| 5,021,059 A | 6/1991 | Kensey et al. |
| 5,108,421 A | 4/1992 | Fowler |
| 5,129,882 A | 7/1992 | Weldon et al. |
| 5,192,300 A | 3/1993 | Fowler |
| 5,192,302 A | 3/1993 | Kensey et al. |
| 5,221,259 A | 6/1993 | Weldon et al. |
| 5,222,974 A | 6/1993 | Kensey et al. |
| 5,254,105 A | 10/1993 | Haaga |
| 5,275,616 A | 1/1994 | Fowler |
| 5,282,827 A | 2/1994 | Kensey et al. |
| 5,290,310 A | 3/1994 | Makower et al. |
| 5,292,332 A | 3/1994 | Lee |
| 5,310,407 A | 5/1994 | Casale |
| 5,312,435 A | 5/1994 | Nash et al. |
| 5,320,639 A | 6/1994 | Rudnick |
| 5,342,393 A | 8/1994 | Stack |
| 5,350,399 A | 9/1994 | Erlebacher et al. |

(Continued)

FOREIGN PATENT DOCUMENTS

EP    1568326 A1    8/2005
EP    1595504 A1    11/2005

(Continued)

*Primary Examiner* — Dianne Dornbusch
*Assistant Examiner* — Robert Lynch
(74) *Attorney, Agent, or Firm* — Seager, Tufte & Wickhem LLC

(57) ABSTRACT

Embodiments of the present disclosure include medical devices and methods including a medical device including: an elongate core element, and a generally tubular torsion element surrounding the core element and capable of transmitting torque along its length. The torsion element has a spiral incision that has a proximal end and a distal end. The spiral incision forms a helically coiled strip between the proximal and distal ends of the spiral incision. The helically coiled strip varies in width from the proximal end of the spiral incision to the distal end of the spiral incision and has a narrowest portion. The helically coiled strip bows radially outward at the narrowest portion when the helically coiled strip in the torsion element is unwound.

8 Claims, 4 Drawing Sheets

(56) References Cited

U.S. PATENT DOCUMENTS

| | | |
|---|---|---|
| 5,370,660 A | 12/1994 | Weinstein et al. |
| 5,383,896 A | 1/1995 | Gershony et al. |
| 5,383,899 A | 1/1995 | Hammerslag |
| 5,391,183 A | 2/1995 | Janzen et al. |
| 5,411,520 A | 5/1995 | Nash et al. |
| 5,413,571 A | 5/1995 | Katsaros et al. |
| 5,415,657 A | 5/1995 | Taymor-Luria |
| 5,419,765 A | 5/1995 | Weldon et al. |
| 5,437,631 A | 8/1995 | Janzen |
| 5,441,517 A | 8/1995 | Kensey et al. |
| 5,443,481 A | 8/1995 | Lee |
| 5,447,502 A | 9/1995 | Haaga |
| 5,454,833 A | 10/1995 | Boussignac et al. |
| 5,478,326 A | 12/1995 | Shiu |
| 5,478,352 A | 12/1995 | Fowler |
| 5,486,195 A | 1/1996 | Myers et al. |
| 5,529,577 A | 6/1996 | Hammerslag |
| 5,531,759 A | 7/1996 | Kensey et al. |
| 5,540,715 A | 7/1996 | Katsaros et al. |
| 5,545,178 A | 8/1996 | Kensey et al. |
| 5,549,633 A | 8/1996 | Evans et al. |
| 5,571,181 A | 11/1996 | Li |
| 5,573,518 A | 11/1996 | Haaga |
| 5,591,204 A | 1/1997 | Janzen et al. |
| 5,593,422 A | 1/1997 | Muijs Van de Moer et al. |
| 5,601,602 A | 2/1997 | Fowler |
| 5,613,974 A | 3/1997 | Andreas et al. |
| 5,620,461 A | 4/1997 | Muijs Van De Moer et al. |
| 5,626,601 A | 5/1997 | Gershony et al. |
| 5,630,833 A | 5/1997 | Katsaros et al. |
| 5,649,959 A | 7/1997 | Hannam et al. |
| 5,653,730 A | 8/1997 | Hammerslag |
| 5,662,681 A | 9/1997 | Nash et al. |
| 5,676,689 A | 10/1997 | Kensey et al. |
| 5,700,277 A | 12/1997 | Nash et al. |
| 5,707,393 A | 1/1998 | Kensey et al. |
| 5,716,375 A | 2/1998 | Fowler |
| 5,725,498 A | 3/1998 | Janzen et al. |
| 5,725,551 A | 3/1998 | Myers et al. |
| 5,728,114 A | 3/1998 | Evans et al. |
| 5,728,122 A | 3/1998 | Leschinsky et al. |
| 5,728,133 A | 3/1998 | Kontos |
| 5,728,134 A | 3/1998 | Barak |
| 5,741,223 A | 4/1998 | Janzen et al. |
| 5,776,142 A | 7/1998 | Gunderson |
| 5,782,860 A | 7/1998 | Epstein et al. |
| 5,810,884 A | 9/1998 | Kim |
| 5,830,130 A | 11/1998 | Janzen et al. |
| 5,843,124 A | 12/1998 | Hammerslag |
| 5,853,421 A | 12/1998 | Leschinsky et al. |
| 5,861,004 A | 1/1999 | Kensey et al. |
| 5,871,474 A | 2/1999 | Hermann et al. |
| 5,871,501 A | 2/1999 | Leschinsky et al. |
| 5,906,631 A | 5/1999 | Imran |
| 5,916,236 A | 6/1999 | Muijs Van de Moer et al. |
| 5,922,009 A | 7/1999 | Epstein et al. |
| 5,935,147 A | 8/1999 | Kensey et al. |
| 5,947,997 A | 9/1999 | Pavcnik et al. |
| 5,948,425 A | 9/1999 | Janzen et al. |
| 5,951,583 A | 9/1999 | Jensen et al. |
| 5,957,952 A | 9/1999 | Gershony et al. |
| 5,964,782 A | 10/1999 | Lafontaine et al. |
| 6,007,561 A | 12/1999 | Bourque et al. |
| 6,017,359 A | 1/2000 | Gershony et al. |
| 6,045,469 A | 4/2000 | Bennett et al. |
| 6,045,569 A | 4/2000 | Kensey et al. |
| 6,045,570 A | 4/2000 | Epstein et al. |
| 6,048,357 A | 4/2000 | Kontos |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,080,183 A | 6/2000 | Tsugita et al. |
| 6,110,184 A | 8/2000 | Weadock |
| 6,120,524 A | 9/2000 | Taheri |
| 6,126,675 A | 10/2000 | Shchervinsky et al. |
| 6,162,240 A | 12/2000 | Cates et al. |
| 6,179,863 B1 | 1/2001 | Kensey et al. |
| 6,183,496 B1 | 2/2001 | Urbanski |
| 6,190,400 B1 | 2/2001 | Van de Moer et al. |
| 6,261,309 B1 | 7/2001 | Urbanski |
| 6,270,515 B1 | 8/2001 | Linden et al. |
| 6,296,632 B1 | 10/2001 | Luscher et al. |
| 6,296,657 B1 | 10/2001 | Brucker |
| 6,296,658 B1 | 10/2001 | Gershony et al. |
| 6,325,789 B1 | 12/2001 | Janzen et al. |
| 6,350,274 B1 | 2/2002 | Li |
| 6,368,300 B1 | 4/2002 | Fallon et al. |
| 6,368,341 B1 | 4/2002 | Abrahamson |
| 6,425,911 B1 | 7/2002 | Akerfeldt et al. |
| 6,461,346 B1 | 10/2002 | Buelna |
| 6,464,712 B1 | 10/2002 | Epstein et al. |
| 6,468,293 B2 | 10/2002 | Bonutti et al. |
| 6,475,177 B1 | 11/2002 | Suzuki |
| 6,475,230 B1 | 11/2002 | Bonutti et al. |
| 6,500,152 B1 | 12/2002 | Illi |
| 6,508,828 B1 | 1/2003 | Akerfeldt et al. |
| 6,524,328 B2 | 2/2003 | Levinson |
| 6,527,734 B2 | 3/2003 | Cragg et al. |
| 6,537,299 B1 | 3/2003 | Hogendijk et al. |
| 6,540,735 B1 | 4/2003 | Ashby et al. |
| 6,562,064 B1 * | 5/2003 | deBeer ........................ 623/1.12 |
| 6,569,187 B1 | 5/2003 | Bonutti et al. |
| 6,572,635 B1 | 6/2003 | Bonutti |
| 6,592,608 B2 | 7/2003 | Fisher et al. |
| 6,596,012 B2 | 7/2003 | Akerfeldt et al. |
| 6,596,014 B2 | 7/2003 | Levinson et al. |
| 6,613,070 B2 | 9/2003 | Redmond et al. |
| 6,623,509 B2 | 9/2003 | Ginn |
| 6,629,981 B2 | 10/2003 | Bui et al. |
| 6,632,238 B2 | 10/2003 | Ginn et al. |
| 6,656,207 B2 | 12/2003 | Taylor et al. |
| 6,663,655 B2 | 12/2003 | Ginn et al. |
| 6,682,489 B2 | 1/2004 | Tenerz et al. |
| 6,685,727 B2 | 2/2004 | Fisher et al. |
| 6,699,261 B1 | 3/2004 | Cates et al. |
| 6,702,846 B2 | 3/2004 | Mikus et al. |
| 6,712,837 B2 | 3/2004 | Åkerfeldt et al. |
| 6,733,515 B1 | 5/2004 | Edwards et al. |
| 6,743,195 B2 | 6/2004 | Zucker |
| 6,749,621 B2 | 6/2004 | Pantages et al. |
| 6,764,500 B1 | 7/2004 | Mujis Van De Moer et al. |
| 6,780,197 B2 | 8/2004 | Roe et al. |
| 6,790,220 B2 | 9/2004 | Morris et al. |
| 6,818,008 B1 | 11/2004 | Cates et al. |
| 6,860,895 B1 | 3/2005 | Akerfeldt et al. |
| 6,863,680 B2 | 3/2005 | Ashby |
| 6,890,342 B2 | 5/2005 | Zhu et al. |
| 6,890,343 B2 | 5/2005 | Ginn et al. |
| 6,896,692 B2 | 5/2005 | Ginn et al. |
| 6,929,655 B2 | 8/2005 | Egnelov et al. |
| 6,939,363 B2 | 9/2005 | Åkerfeldt |
| 6,942,684 B2 | 9/2005 | Bonutti |
| 6,955,683 B2 | 10/2005 | Bonutti |
| 6,964,658 B2 | 11/2005 | Ashby et al. |
| 6,969,397 B2 | 11/2005 | Ginn |
| 7,001,398 B2 | 2/2006 | Carley et al. |
| 7,008,439 B1 | 3/2006 | Janzen et al. |
| 7,008,440 B2 | 3/2006 | Sing et al. |
| 7,008,441 B2 | 3/2006 | Zucker |
| 7,008,442 B2 | 3/2006 | Brightbill |
| 7,025,776 B1 | 4/2006 | Houser et al. |
| 7,037,323 B2 | 5/2006 | Sing et al. |
| 7,044,916 B2 | 5/2006 | Tenerz et al. |
| 7,083,635 B2 | 8/2006 | Ginn |
| 7,192,436 B2 | 3/2007 | Sing et al. |
| 7,267,679 B2 | 9/2007 | McGuckin, Jr. et al. |
| 7,316,704 B2 | 1/2008 | Bagaoisan et al. |
| 7,322,976 B2 | 1/2008 | Yassinzadeh |
| 7,331,979 B2 | 2/2008 | Khosravi et al. |
| 7,331,981 B2 | 2/2008 | Cates et al. |
| 7,335,220 B2 | 2/2008 | Khosravi et al. |
| 2002/0002889 A1 | 1/2002 | Ashby et al. |
| 2002/0016612 A1 | 2/2002 | Ashby et al. |

(56) References Cited

U.S. PATENT DOCUMENTS

| | | |
|---|---|---|
| 2002/0198562 A1 | 12/2002 | Akerfeldt et al. |
| 2003/0088271 A1 | 5/2003 | Cragg et al. |
| 2004/0093025 A1 | 5/2004 | Egnelov |
| 2004/0098044 A1 | 5/2004 | Van de Moer et al. |
| 2004/0098046 A1 | 5/2004 | Tenerz et al. |
| 2004/0172059 A1 | 9/2004 | Tenerz et al. |
| 2004/0204741 A1 | 10/2004 | Egnelov et al. |
| 2004/0215232 A1 | 10/2004 | Belhe et al. |
| 2004/0243007 A1 | 12/2004 | Tenerz et al. |
| 2005/0010248 A1 | 1/2005 | Lafontaine |
| 2005/0049637 A1 | 3/2005 | Morris et al. |
| 2005/0085852 A1 | 4/2005 | Ditter |
| 2005/0085855 A1 | 4/2005 | Forsberg |
| 2005/0096498 A1 | 5/2005 | Houser et al. |
| 2005/0096696 A1 | 5/2005 | Forsberg |
| 2005/0096697 A1 | 5/2005 | Forsberg et al. |
| 2005/0107827 A1 | 5/2005 | Paprocki |
| 2005/0125031 A1 | 6/2005 | Pipenhagen et al. |
| 2005/0137624 A1 | 6/2005 | Fallman |
| 2005/0169974 A1 | 8/2005 | Tenerz et al. |
| 2005/0177189 A1 | 8/2005 | Ginn et al. |
| 2005/0267521 A1 | 12/2005 | Forsberg |
| 2005/0267528 A1 | 12/2005 | Ginn et al. |
| 2006/0004408 A1 | 1/2006 | Morris et al. |
| 2006/0030886 A1 | 2/2006 | Clark |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0100664 A1 | 5/2006 | Pai et al. |
| 2006/0136034 A1* | 6/2006 | Modesitt et al. ............ 623/1.11 |
| 2006/0142797 A1 | 6/2006 | Egnelov |
| 2006/0173492 A1 | 8/2006 | Akerfeldt et al. |
| 2006/0178682 A1 | 8/2006 | Boehlke |
| 2006/0206146 A1 | 9/2006 | Tenerz |
| 2006/0229672 A1 | 10/2006 | Forsberg |
| 2006/0229673 A1 | 10/2006 | Forsberg |
| 2006/0229674 A1 | 10/2006 | Forsberg |
| 2006/0265006 A1 | 11/2006 | White et al. |
| 2006/0265007 A1 | 11/2006 | White et al. |
| 2006/0265008 A1 | 11/2006 | Maruyama et al. |
| 2007/0032823 A1 | 2/2007 | Tegg |
| 2007/0032824 A1 | 2/2007 | Terwey |
| 2007/0038244 A1 | 2/2007 | Morris et al. |
| 2007/0038245 A1 | 2/2007 | Morris et al. |
| 2007/0073345 A1 | 3/2007 | Pipenhagen et al. |
| 2007/0083231 A1 | 4/2007 | Lee |
| 2007/0083232 A1 | 4/2007 | Lee |
| 2007/0135842 A1 | 6/2007 | Van de Moer et al. |
| 2007/0276433 A1 | 11/2007 | Huss |
| 2008/0065121 A1 | 3/2008 | Kawaura et al. |
| 2008/0071311 A1 | 3/2008 | White et al. |
| 2008/0097521 A1 | 4/2008 | Khosravi et al. |
| 2008/0109030 A1 | 5/2008 | Houser et al. |
| 2008/0114394 A1 | 5/2008 | Houser et al. |
| 2009/0024106 A1 | 1/2009 | Morris |
| 2009/0088794 A1 | 4/2009 | LaFontaine |
| 2010/0217311 A1 | 8/2010 | Jenson et al. |
| 2011/0066181 A1 | 3/2011 | Jenson et al. |
| 2011/0190865 A1 | 8/2011 | McHugo et al. |
| 2011/0295354 A1 | 12/2011 | Bueche et al. |

FOREIGN PATENT DOCUMENTS

| | | | |
|---|---|---|---|
| EP | 1671591 | A1 | 6/2006 |
| WO | 8911301 | A1 | 11/1989 |
| WO | 02096295 | A1 | 12/2002 |
| WO | 2004093649 | A2 | 11/2004 |
| WO | 2006078578 | A2 | 7/2006 |
| WO | 2006124238 | A2 | 11/2006 |
| WO | 2007025019 | A2 | 3/2007 |

* cited by examiner

TORQUE MECHANISM ACTUATED BIOABSORBABLE VASCULAR CLOSURE DEVICE

PRIORITY

This application claims priority under 35 U.S.C. §119 to U.S. Provisional Application Ser. No. 61/383,827 entitled "TORQUE MECHANISM ACTUATED BIOABSORBABLE VASCULAR CLOSURE DEVICE" filed Sep. 17, 2010, the entirety of which is incorporated herein by reference.

FIELD

The present disclosure relates generally to medical devices and, more particularly, to methods and devices for producing controllable radial expansion and/or contraction of an intravessel element for hemostasis.

BACKGROUND

For various medical procedures, such as hemostasis, a device is inserted into the vasculature of a patient, is fed through the vasculature to a desired location within a vessel, and then expands radially. For hemostasis, the radial expansion of the device may deliver an expandable plug to a wound or opening in the vessel. For other procedures, such as stent delivery, the radial expansion of the device may force an expandable stent radially outward onto the interior wall of the vessel. Once radial expansion of the device is accomplished, the device may retract radially, optionally leaving the expanded plug or stent in place at the desired location in the vessel, and may be withdrawn from the vasculature of the patient.

There is an ongoing effort to improve various aspects of these procedures, including elements that can radially expand to deliver, for example, a plug or stent.

BRIEF SUMMARY

An illustrative embodiment of the present disclosure is a medical device including: an elongate core element, and a generally tubular torsion element surrounding the core element and capable of transmitting torque along its length. The torsion element has a spiral incision that has a proximal end and a distal end. The spiral incision forms a helically coiled strip between the proximal and distal ends of the spiral incision. The helically coiled strip varies in width from the proximal end of the spiral incision to the distal end of the spiral incision and has a narrowest portion. The helically coiled strip bows radially outward at the narrowest portion when the helically coiled strip in the torsion element is unwound.

Another illustrative embodiment of the present disclosure is a medical device, including: a handle having a depressible push button, a catheter extending distally from the handle and comprising a torsion element and a rotational anchor, a plunger extending distally from the push button, a threaded interface for converting a linear motion of the plunger into a rotation of the torsion element with respect to the rotational anchor, a helically coiled strip within the catheter and proximate a distal end of the catheter, wherein rotation of the torsion element with respect to the rotational anchor uncoils at least a portion of the helically coiled strip and produces radial expansion of the portion of the helically coiled strip, and a radially expandable element radially surrounding the portion of the helically coiled strip.

Another illustrative embodiment of the present disclosure is a method for radially expanding an expandable element in a medical device, including: receiving a linear depression of a push button, converting the linear depression into a rotation, transmitting the rotation to one end of a helically coiled strip, the other end of the helically coiled strip being rotationally fixed, uncoiling a portion of the helically coiled strip, the uncoiled portion bowing radially outward, and radially expanding an expandable element disposed radially around the portion of helically coiled strip.

The preceding summary is provided to facilitate an understanding of some of the innovative features unique to the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following detailed description of various illustrative embodiments of the disclosure in connection with the accompanying drawings, in which.

DETAILED DESCRIPTION

Figure 1:
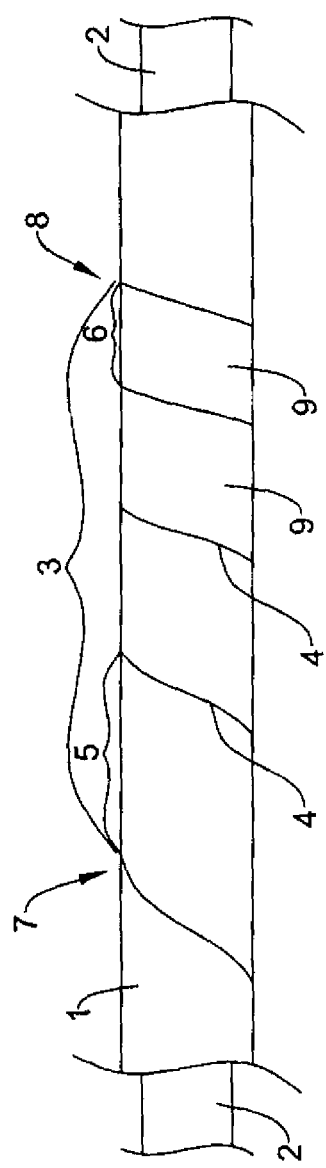
FIG. 1 is a schematic drawing of a torsion element surrounding a core element, where the helically coiled strip on the torsion element is in a radially unexpanded state.

The following description should be read with reference to the drawings wherein like reference numerals indicate like elements throughout the several views. The detailed description and drawings, which are not necessarily drawn to scale, show several embodiments which are meant to be illustrative and are not intended to limit the scope of the disclosure.

For various medical procedures, such as hemostasis, a device is inserted into the vasculature of a patient, is fed through the vasculature to a desired location within a vessel, and then expands radially. For hemostasis, the radial expansion of the device may deliver an expandable plug to a wound or opening in the vessel. For other procedures, such as stent delivery, the radial expansion of the device may force an expandable stent radially outward onto the interior wall of the vessel. Once radial expansion of the device is accomplished, the device may retract radially, optionally leaving the expanded plug or stent in place at the desired location in the vessel, and may be withdrawn from the vasculature of the patient.

For the designs presented herein, the element that performs the radial expansion includes a tube having a spiral incision that forms a longitudinal portion of the tube into a helically coiled strip. In its nominal state, the helically coiled strip is the same size and shape as the rest of the tube. In its radially expanded state, a portion of the helically coiled member is rotationally partially "unwound", which produces an outward bowing and, therefore, a radial expansion in the "unwound" portion of the helically coiled strip.

In some cases, the torque required to produce such an unwinding may be transmitted between the tube and a core member that passes through the interior of the tube. Alternatively, the torque may be transmitted between the tube and the wall of the vessel itself, or between the tube and another device separate from the tube.

Figure 2:
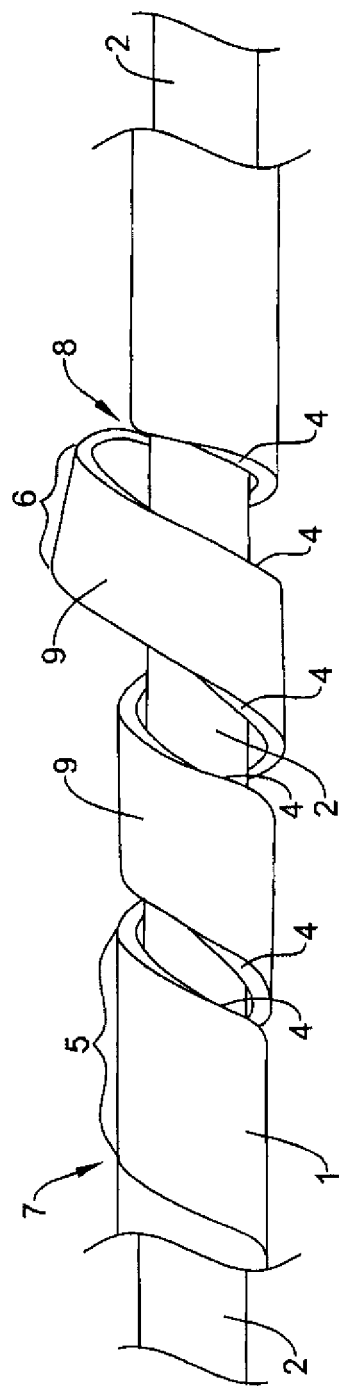
FIG. 2 is a schematic drawing of the torsion element and core element of FIG. 1, with a portion of the helically coiled strip on the torsion element being partially unwound in the radially expanded state.

FIG. 1 is a schematic drawing of a torsion element 1 surrounding a core element (disposed inside the torsion element 1 and not visible in FIG. 1), where the torsion element 1 is in a radially unexpanded, or relaxed state. FIG. 2 is a schematic drawing of the torsion element 1 and core element 2 of FIG. 1, with a portion of the torsion element 1 being partially unwound in the radially expanded state.

The torsion element 1 surrounds the core element 2, where the torsion element 1 has an inside diameter equal to or larger than an outside diameter of the core element 2. The core element 2 may be an elongated wire, a tube, a slotted tube, a ribbon, or other suitable shape that is capable of transmitting torque from a proximal end to a distal end. The proximal end of the torsion element 1 remains outside the patient, and is typically under the control of a practitioner throughout the procedure. The proximal end of the torsion element 1 may include a handle and/or various other controls, which are not shown in FIGS. 1 and 2. The distal end of the torsion element 1 is fed through a vasculature of a patient to a desired location, such as a blockage or an opening to be closed.

For the exemplary design of FIGS. 1 and 2, the torsion element 1 is formed as a hollow tube having a spiral incision 4. The spiral incision 4 forms a helically coiled strip 9 in the tube. In FIG. 1, where the torsion element 1 is in its relaxed state, the spiral incision 4 subtends about four rotations around the element 1. In FIG. 2, where the torsion element 1 is in its radially expanded state, the proximal end 7 of the spiral incision 4 has been rotated counterclockwise (looking end-on from the proximal end 7) by about one full rotation, with respect to the distal end 8 of the spiral incision 4. Note in FIG. 2 that in the radially expanded state, the spiral incision 4 now subtends only about three full rotations, compared to four rotations in the unexpanded state of FIG. 1. In FIG. 2, the helically coiled portion 3 of the torsion element 1 has been "unwound" by about one full rotation.

It will be understood that the spiral incision length of four circumferential rotations and the "unwinding" length of one circumferential rotation are merely examples, and are not intended to be limiting in any way. Other circumferential rotational values may also be used, including spiral incision lengths (in units of circumferential rotations) having 0.25, 0.5, 0.75, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, or any other suitable value. Other "unwinding" values, expressed as a percentage of the unwound spiral incision length, are 10 percent, 15 percent, 20 percent, 25 percent, 30 percent, 35 percent, 40 percent, 45 percent, 50 percent, or any other suitable value.

In FIGS. 1 and 2, the spiral incision 4 and helically coiled strip 9 have a particular handedness, so that looking end-on from the proximal end 7, counterclockwise rotation of the proximal end 7, with respect to a fixed distal end 8, produces "uncoiling" or "unraveling" of the helically coiled strip 9, and radially outward bowing of the helically coiled strip 9. Alternatively, the handedness of the spiral incision 4 and the helically coiled strip 9 may be reversed, so that clockwise, rather than counterclockwise, rotation produces the radially outward bowing.

Note that in FIG. 1, the spiral incision 4 is not truly helical, but varies slightly in inclination from the proximal (leftmost) end 7 to the distal (rightmost) end 8, so that the helically coiled strip 9 of material becomes thinner at the distal end 6 than at the proximal end 5. This variation may be useful in determining where the "uncoiling" or "unraveling" occurs; the thinnest part of the helically coiled strip 9 of material unravels first. Note in FIG. 2 that the relatively thin distal end 6 bows radially outward, while the relatively thick proximal end 5 shows little to no bowing. Although the example design of FIGS. 1 and 2 show the helically coiled strip 9 being thinner at the distal end 6 than at the proximal end 5, the variation may be reversed, so that the helically coiled strip 9 is thinner at the proximal end 7 than at the distal end 8. In many cases, the helically coiled strip 9 width varies monotonically from the proximal end 7 to the distal end 8. In some cases, the helically coiled strip 9 width decreases by a particular percentage from one end to the other, such as 30 percent, 40 percent, 50 percent, 60 percent, 70 percent, or other suitable value. As a further alternative, the helically coiled strip 9 may be thinner at its center than at its longitudinal ends. In general, the radially outward bowing shows up first at the thinnest portion of the helically coiled strip 9, and it may be desirable to locate this thinnest portion of the helically coiled strip 9 at the radially expandable element, such as the expanding plug or the expanding stent. Alternatively, the spiral incision 4 may be truly helical, and the helically coiled strip 9 may have a uniform width from its proximal end 7 to its distal end 8.

The uncoiling of the helically coiled strip 9 may require rotation of a proximal portion of the torsion element 1 with respect to a distal portion of the torsion element 1. In general, the torsion element 1 may be a tube that can transmit rotation, so that if the torsion element 1 is rotated proximally, such as at or near the handle, the rotation may be transmitted to the proximal end of the spiral incision 4. As such, the torsion element 1 may be anchored at one end, such as at its distal end or its proximal end, and may be rotatable at the opposite end. In some cases, the torsion element 1 is rotationally anchored to the core element 2 at their respective distal ends. In other cases, the anchoring may be done at the proximal ends, or at a point between the distal and proximal ends.

Alternatively, there may be more than one spiral incision 4.

Figure 3:
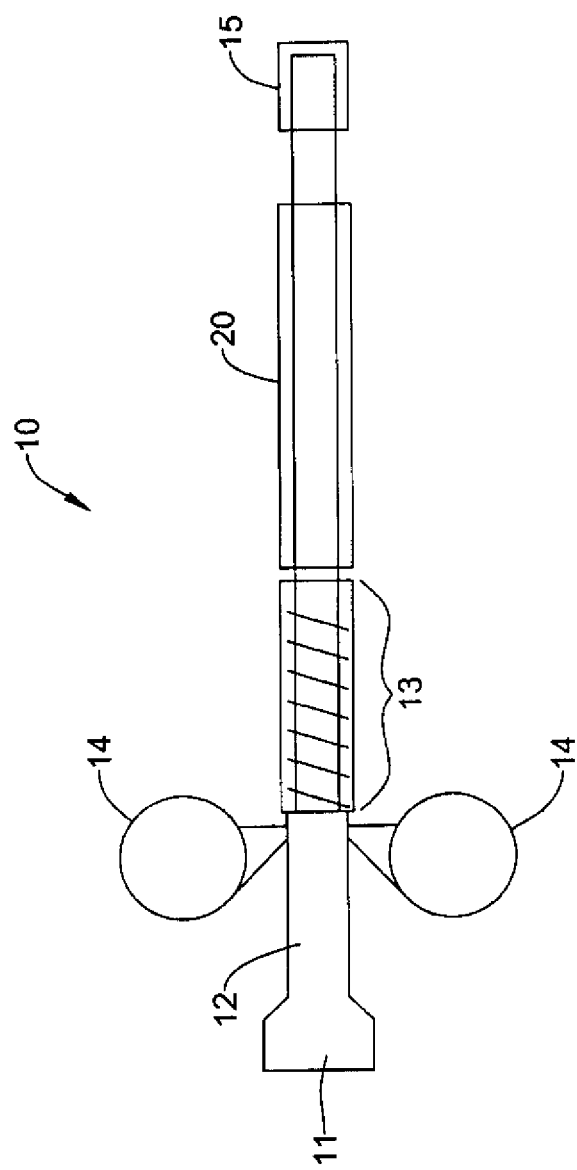
FIG. 3 is a schematic drawing of a system that incorporates the radially expandable elements of FIGS. 1 and 2, in the unexpanded state.
Figure 4:
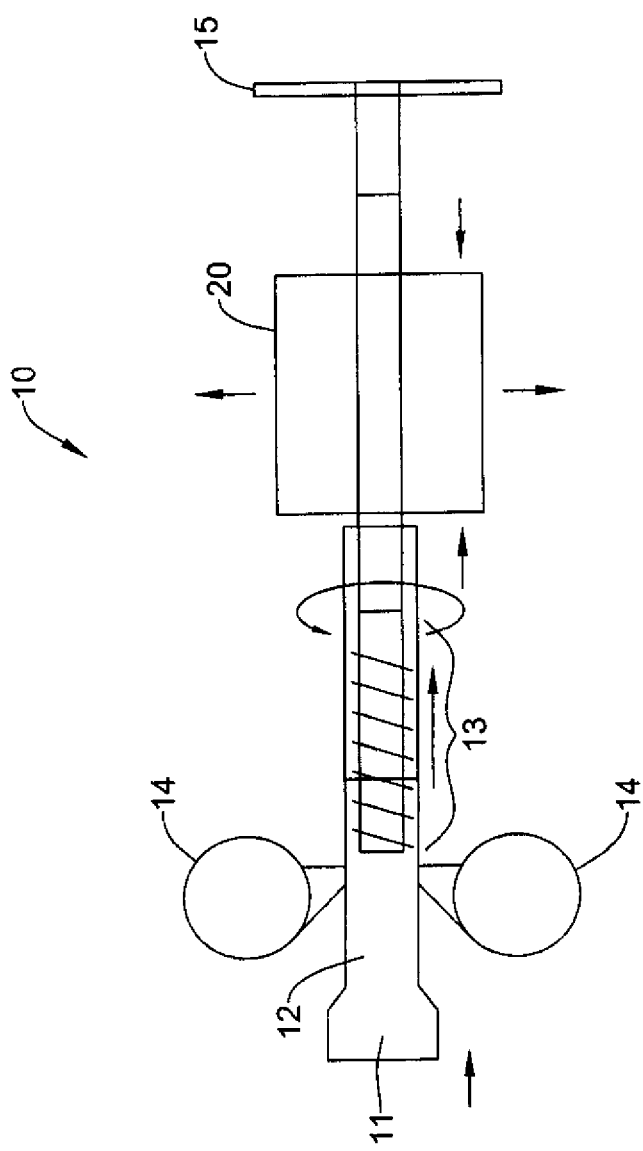
FIG. 4 is a schematic drawing of a system that incorporates the radially expandable elements of FIGS. 1 and 2, in the radially expanded state.

FIGS. 3 and 4 are schematic drawings of a device 10 that incorporates the radially expanding elements shown in FIGS. 1 and 2. Such a device 10 may use the same "unwinding" of an element to achieve the radial expansion, but may have a more convenient interface for the practitioner. For instance, the exemplary design of FIGS. 3 and 4 shows a handle having a push button interface, where depressing the push button 11 produces a radial expansion of the expandable element 20. Optionally, withdrawing of the push button 11 may decrease the radial expansion, in some cases to the pre-expansion level, so that the device 10 may be withdrawn from the vasculature of the patient.

For the device 10 of FIGS. 3 and 4, the push button 11 mechanism converts a linear displacement or linear translation into a rotation or rotational displacement. The rotation is transmitted from the push button 11 mechanism, along the torsion element 1, to the spiral incision 4 and the helically coiled strip 9 formed in the torsion element 1. In many cases, the rotation is imparted to the proximal end of the torsion element 1, while the core element 2 remains rotationally stationary. In other cases, the rotation is imparted to the core element 2, while the proximal end of the torsion element 1 remains rotationally stationary. In both of these cases, the torsion element 1 and the core element 2 are rotationally joined at a point distal to the distal end of the spiral incision 4, such as the distal ends of both elements. Both may be joined to each other at a vessel anchor 15, which may help reduce or eliminate longitudinal motion of the device 10 with respect to its target location within the vessel.

The torsion generated by the push button 11 may be actuated by a threaded interface, where the threads have a relatively low pitch. When the practitioner depresses the button by a predefined amount, such as 1 centimeter (cm) or 2 cm, the threads force the torsion element 1 or core element 2 to rotate by a predefined amount, such as 1 revolution.

Note that for this threaded interface, the thread pitch (number of threads per inch, or threads per cm), is significantly lower than for typical threaded fasteners, such as wood screws. For a typical wood screw, a user applies a torque on the screw head, which is converted into a linear translation. For wood screws, a relatively large rotation produces a relatively small translation. Note that a typical wood screw would not work for the threaded interface discussed herein because the thread pitch is too high. One cannot force rotation of a wood screw just by pushing on the screw head, because the static frictional force at the screw threads is too large and prevents rotation.

For the threaded interface of the present disclosure, the thread pitch should be low enough so that one may achieve a conversion of translation-to-rotation without being impaired by static frictional forces at the threads. Common thread pitches (in units of threads/cm) may include 0.25, 0.5, 0.75, 1, 1.25, 1.5, 1.75, 2, 2.25, 2.5, 2.75, 3, or other suitable value.

In the exemplary design of FIGS. 3 and 4, the push button 11 is attached to or made integral with a plunger 12. The plunger 12 has a threaded interface 13 that mates it with, for example, the torsion element 1 or the core element 2. When the push button 11 is depressed, the plunger 13 is forced distally, and the threaded interface forces the torsion element 1, or the core element 2, to rotate with respect to the core element 2, or the torsion element 1, respectively.

Alternatively, the handle may be configured so that a withdrawal of the push button 11 produces a radial expansion at the implantable component, rather than a depression of the push button 11.

The handle of the device 10 may optionally include one or more thumb holes 14.

The exemplary design of FIGS. 3 and 4 includes an implantable component, such as expanding plug 20. Although FIGS. 3 and 4 illustrate the implantable component as being an expanding plug, the implantable element can also be an anchor, a stent, or other suitable device. In some cases, it is desirable that the implantable component be at least partially bioabsorbable. Such implantable components may be formed from metal, polymers, for example, PLGA and PLA, collagen, magnesium, tyrosine derived polycarbonate, or other suitable material or combination of materials.

Having thus described the preferred embodiments of the present disclosure, those of skill in the art will readily appreciate that other embodiments may be made and used within the scope of the claims hereto attached. Numerous advantages of the disclosure covered by this document have been set forth in the foregoing description. It will be understood, however, that this disclosure is, in many respect, only illustrative. Changes may be made in details, particularly in matters of shape, size, and arrangement of parts without exceeding the scope of the disclosure. The invention's scope is, of course, defined in the language in which the appended claims are expressed.

What is claimed is:

1. A medical device, comprising:
   a handle having a depressible push button;
   a catheter extending distally from the handle and comprising a torsion element and a rotational anchor;
   a plunger extending distally from the push button;
   a threaded interface for converting a linear motion of the plunger into a rotation of the torsion element with respect to the rotational anchor;
   a helically coiled strip within the catheter and proximate a distal end of the catheter, wherein rotation of the torsion element with respect to the rotational anchor uncoils at least a portion of the helically coiled strip and produces radial expansion of the portion of the helically coiled strip; and
   a radially expandable element radially surrounding the portion of the helically coiled strip.

2. The medical device of claim 1, wherein the radially expandable element is an expanding plug.

3. The medical device of claim 1, wherein the radially expandable element is an expandable stent.

4. The medical device of claim 1, wherein the helically coiled strip is defined by a spiral incision on the torsion element.

5. The medical device of claim 1, wherein the torsion element is a tube surrounding the rotational anchor.

6. The medical device of claim 1, wherein the torsion element is rotationally attached to the rotational anchor at at least one point distal to the helically coiled strip.

7. The medical device of claim 1, wherein the threaded interface includes threads having a pitch low enough to overcome static frictional forces.

8. A method for radially expanding an expandable element in a medical device, comprising:
   receiving a linear depression of a push button from a practitioner;
   converting the linear depression into a rotation;
   transmitting the rotation to one end of a helically coiled strip, the other end of the helically coiled strip being rotationally fixed;
   uncoiling a portion of the helically coiled strip, the uncoiled portion bowing radially outward; and
   radially expanding an expandable element disposed radially around the portion of helically coiled strip.

* * * * *